(12) United States Patent
Petcavich

(10) Patent No.: US 11,248,212 B2
(45) Date of Patent: Feb. 15, 2022

(54) SURFACE ENERGY DIRECTED CELL SELF ASSEMBLY

(71) Applicant: StemoniX Inc., Eden Prairie, MN (US)

(72) Inventor: Robert John Petcavich, The Woodlands, TX (US)

(73) Assignee: StemoniX Inc., Eden Prairie, MN (US)

( * ) Notice: Subject to any disclaimer, the term of this patent is extended or adjusted under 35 U.S.C. 154(b) by 0 days.

(21) Appl. No.: 15/199,419

(22) Filed: Jun. 30, 2016

(65) Prior Publication Data

US 2017/0002324 A1    Jan. 5, 2017

Related U.S. Application Data

(60) Provisional application No. 62/186,670, filed on Jun. 30, 2015.

(51) Int. Cl.
*C12N 5/077*    (2010.01)

(52) U.S. Cl.
CPC ........ *C12N 5/0657* (2013.01); *C12N 2506/45* (2013.01); *C12N 2521/00* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 5,260,210 A | 11/1993 | Rubin et al. | |
| 5,981,268 A | 11/1999 | Kovacs et al. | |
| 6,565,813 B1* | 5/2003 | Garyantes | B01F 13/0071 422/553 |
| 10,625,234 B2 | 4/2020 | Petcavich | |
| 10,760,053 B2 | 9/2020 | Petcavich | |
| 2002/0049160 A1 | 4/2002 | Huang et al. | |
| 2004/0067546 A1 | 4/2004 | Leng et al. | |
| 2005/0169962 A1 | 8/2005 | Bhatia et al. | |
| 2007/0017530 A1 | 1/2007 | Syed et al. | |
| 2007/0122392 A1 | 5/2007 | Gerecht-nir et al. | |
| 2007/0280987 A1 | 12/2007 | Heimus et al. | |
| 2008/0009517 A1 | 1/2008 | Gupta et al. | |
| 2008/0193536 A1 | 8/2008 | Khademhosseini et al. | |
| 2010/0055733 A1 | 3/2010 | Lutolf et al. | |
| 2010/0120626 A1 | 5/2010 | Ross et al. | |
| 2010/0233750 A1 | 9/2010 | Couraud et al. | |
| 2010/0317103 A1 | 12/2010 | Cho et al. | |
| 2011/0306041 A1 | 12/2011 | Viovy et al. | |
| 2012/0015395 A1 | 1/2012 | Shusta et al. | |
| 2012/0053084 A1 | 3/2012 | Gerber et al. | |
| 2012/0149781 A1 | 6/2012 | Lee et al. | |
| 2012/0302467 A1* | 11/2012 | Levkin | C12N 5/0068 506/26 |
| 2012/0308531 A1 | 12/2012 | Pinxteren et al. | |
| 2013/0029421 A1* | 1/2013 | Komvopoulos | C12N 5/0068 435/396 |
| 2013/0034904 A1 | 2/2013 | Fan et al. | |
| 2013/0171116 A1 | 7/2013 | Shoham et al. | |
| 2013/0203086 A1 | 8/2013 | Achyuta et al. | |
| 2013/0217113 A1 | 8/2013 | Srinivasan et al. | |
| 2014/0142370 A1 | 5/2014 | Wong et al. | |
| 2014/0287506 A1 | 9/2014 | Sanyal et al. | |
| 2015/0301028 A1 | 10/2015 | Eggan et al. | |
| 2016/0059203 A1 | 3/2016 | Petcavich | |
| 2017/0107488 A1 | 4/2017 | Petcavich | |
| 2017/0166857 A1 | 6/2017 | Petcavich | |
| 2018/0113118 A1 | 4/2018 | Petcavich | |
| 2018/0291336 A1 | 10/2018 | Petcavich | |
| 2019/0161717 A1 | 5/2019 | Petcavich | |
| 2019/0177691 A1 | 6/2019 | Petcavich | |
| 2020/0353438 A1 | 11/2020 | Petcavich | |
| 2021/0062147 A1 | 3/2021 | Petcavich | |

FOREIGN PATENT DOCUMENTS

| | | |
|---|---|---|
| CN | 102156158 A | 8/2011 |
| DE | 102014003465 A1 | 9/2015 |
| JP | 2003503715 A | 1/2003 |
| JP | 2005505747 A | 2/2005 |
| JP | 2007516699 A | 6/2007 |
| JP | 2008199962 A | 9/2008 |
| JP | 2013/135685 A | 7/2013 |
| JP | 2014519825 A | 8/2014 |
| JP | 2017532061 A | 11/2017 |
| JP | 2018536424 A | 12/2018 |
| JP | 2018537073 A | 12/2018 |
| WO | WO-2011/088213 A1 | 7/2011 |
| WO | WO-2012168295 A1 | 12/2012 |

(Continued)

OTHER PUBLICATIONS

US 10,562,004 B2, 02/2020, Petcavich (withdrawn)
Cwikel, D. et al. 2010. Comparing contact angle measurements and surface tension assessments of solid surfaces. Langmuir 26(19): 15289-15294. specif, p. 15289.*
Ueda, Y. et al. 2012. Substrates for human pluripotent stem cell cultures in conditioned medium of mesenchymal stem cells. Journal of Biomaterials Science 23: 153-165. specif. pp. 153, 154, 159.*
Kim, D-H. et al. 2006. Guided three-dimensional growth of functional cardiomyocytes on polyethylene glycol nanostructures. Langmuir 22: 5419-5426. specif. pp. 5419, 5425, 5426.*
Jing, G. et al. 2011. Cell patterning using molecular vapor deposition of self-assembled monolayers and lift-off technique. Acta Biomaterialia 7: 1094-1103. specif. pp. 1095, 1096, 1097, 1099, 1100.*

(Continued)

*Primary Examiner* — Lynn Y Fan
*Assistant Examiner* — Sharon M. Papciak
(74) *Attorney, Agent, or Firm* — Schwegman Lundberg & Woessner, P.A.

(57) ABSTRACT

The present disclosure provides a method of fabricating cell, such as stem cell, arrays on a carrier where the surface energy of the carrier has been modified and patterned so that only areas of low contact angle are wetted by a water based cell solution. The patterned cell solution when applied to the carrier surface then self assembles into a 3 dimensional micro pattern on the carrier that mimics the surface topography of mammalian organs.

17 Claims, 5 Drawing Sheets

(56) References Cited

FOREIGN PATENT DOCUMENTS

| WO | WO-2014063194 A1 | 5/2014 |
|---|---|---|
| WO | WO-2014110559 A1 | 7/2014 |
| WO | WO-2014/145975 A2 | 9/2014 |
| WO | WO-2014144219 A1 | 9/2014 |
| WO | WO-2015/069943 A1 | 5/2015 |
| WO | WO-201 6033501 A1 | 3/2016 |
| WO | WO-2016090486 A1 | 6/2016 |
| WO | WO-201 7066663 A1 | 4/2017 |
| WO | WO-2017100705 A1 | 6/2017 |
| WO | WO-2018026925 A1 | 2/2018 |
| WO | WO-2018026929 A1 | 2/2018 |
| WO | WO-2018075890 A1 | 4/2018 |

OTHER PUBLICATIONS

Yuan, Y. et al. Contact angle and wetting properties. In: Surface Scientific Techniques. Chapter 1. Copyright 2013 Springer-Verlag, Berlin/Heidelberg. Eds.: Bracco, G & Holst, B. pp. 3-34. specif. pp. 3, 4, 23.*
Cooke, M.J. et al. 2008. Enhanced cell attachment using a novel cell culture surface presenting functional domains from extracellular matrix proteins. Cytotechnology 56: 71-79. specif. p. 71.*
Geyer, Florian L, et al., "Superhydrophobic-Superhydrophilic Micropatterning: Towards Genome-on-a-Chip Cell Microarrays", Angewandte Chemie International Edition, vol. 50, Issue 36, (2011), pp. 8424-8427.
"U.S. Appl. No. 14/839,170, Advisory Action dated Jun. 5, 2018", 4 pgs.
"U.S. Appl. No. 14/839,170, Final Office Action dated Jan. 30, 2019", 19 pgs.
"U.S. Appl. No. 14/839,170, Final Office Action dated Mar. 12, 2018", 12 pgs.
"U.S. Appl. No. 14/839,170, Non Final Office Action dated Feb. 9, 2017", 8 pgs.
"U.S. Appl. No. 17/839,170, Non Final Office Action dated Sep. 7, 2018", 19 pgs.
"U.S. Appl. No. 14/839,170, Response filed Jan. 7, 2019 to Non Final Office Action dated Sep. 7, 2018", 10 pgs.
"U.S. Appl. No. 14/839,170, Response filed Jan. 11, 2017 to Restriction Requirement dated Nov. 18, 2016", 6 pgs.
"U.S. Appl. No. 14/839,170, Response filed May 9, 2017 to Non Final Office Action dated Feb. 9, 2017", 7 pgs.
"U.S. Appl. No. 14/839,170, Response filed May 14, 2018 to Final Office Action dated Mar. 12, 2018", 7 pgs.
"U.S. Appl. No. 14/839,170, Response filed Jul. 12, 2018 to Final Office Action dated Mar. 12, 2018", 7 pgs.
"U.S. Appl. No. 14/839,170, Restriction Requirement dated Nov. 18, 2016", 6 pgs.
"U.S. Appl. No. 15/293,563, Final Office Action dated Apr. 3, 2019", 11 pgs.
"U.S. Appl. No. 15/293,563, Non Final Office Action dated Nov. 29, 2018", 11 pgs.
"U.S. Appl. No. 15/293,563, Response filed Feb. 26, 2019 to Non Final Office Action dated Nov. 29, 2018", 6 pgs.
"U.S. Appl. No. 15/293,563, Response filed Sep. 12, 2018 to Restriction Requirement dated Jul. 16, 2018", 5 pgs.
"U.S. Appl. No. 15/293,563, Restriction Requirement dated Jul. 16, 2018", 6 pgs.
"U.S. Appl. No. 15/374,961, Non Final Office Action dated Nov. 30, 2018", 15 pgs.
"U.S. Appl. No. 15/374,961, Response filed Feb. 28, 2019 to Non Final Office Action dated Nov. 30, 2018", 7 pgs.
"U.S. Appl. No. 15/374,961, Response filed Oct. 2, 2018 to Restriction Requirement dated Aug. 2, 2018", 6 pgs.
"U.S. Appl. No. 15/374,961, Restriction Requirement dated Aug. 2, 2018", 7 pgs.
"U.S. Appl. No. 15/789,335, Response filed Apr. 8, 2019 to Restriction Requirement dated Feb. 7, 2019", 5 pgs.
"U.S. Appl. No. 15/789,335, Restriction Requirement dated Feb. 7, 2019", 8 pgs.
"European Application Serial No. 15762878.5, Communication Pursuant to Article 94(3) EPC dated Jan. 4, 2018", 5 pgs.
"European Application Serial No. 15762878.5, Communication Pursuant to Article 94(3) EPC dated Nov. 20, 2018", 4 pgs.
"European Application Serial No. 15762878.5, Response filed Jul. 16, 2018 to Communication Pursuant to Article 94(3) EPC dated Jan. 4, 2018", 34 pgs.
"European Application Serial No. 15762878.5, Response filed Oct. 16, 2017 to Communication pursuant to Rules 161(1) and 162 EPC dated Apr. 4, 2017", 9 pgs.
"European Application Serial No. 16829018.7, Response filed Feb. 5, 2019 to Communication Pursuant to Rules 161(1) and 162 EPC dated Jul. 26, 2019", 8 pgs.
"International Application Serial No. PCT/US15/47494, International Search Report dated Nov. 6, 2015", 4 pgs.
"International Application Serial No. PCT/US15/47494, Written Opinion dated Nov. 6, 2015", 6 pgs.
"International Application Serial No. PCT/US2015/047494, International Preliminary Report on Patentability dated Mar. 9, 2017", 8 pgs.
"International Application Serial No. PCT/US2016/057172, International Preliminary Report on Patentability dated Apr. 26, 2018", 7 pgs.
"International Application Serial No. PCT/US2016/057172, International Search Report dated Jan. 17, 2017", 5 pgs.
"International Application Serial No. PCT/US2016/057172, International Written Opinion dated Jan. 17, 2017", 5 pgs.
"International Application Serial No. PCT/US2016/066014, International Preliminary Report on Patentability dated Jun. 21, 2018", 8 pgs.
"International Application Serial No. PCT/US2016/066014, International Search Report dated Apr. 5, 2017", 5 pgs.
"International Application Serial No. PCT/US2016/066014, Written Opinion dated Apr. 5, 2017", 9 pgs.
"International Application Serial No. PCT/US2017/045114, International Preliminary Report on Patentability dated Feb. 14, 2019", 9 pgs.
"International Application Serial No. PCT/US2017/045114, International Search Report dated Oct. 23, 2017", 5 pgs.
"International Application Serial No. PCT/US2017/045114, Written Opinion dated Oct. 23, 2017", 7 pgs.
"International Application Serial No. PCT/US2017/045119, International Preliminary Report on Patentability dated Feb. 14, 2019", 8 pgs.
"International Application Serial No. PCT/US2017/045119, International Search Report dated Oct. 27, 2017", 3 pgs.
"International Application Serial No. PCT/US2017/045119, Written Opinion dated Oct. 27, 2017", 6 pgs.
"International Application Serial No. PCT/US2017/057591, International Search Report dated Jan. 30, 2018", 6 pgs.
"International Application Serial No. PCT/US2017/057591, Written Opinion dated Jan. 30, 2018", 5 pgs.
"Japanese Application Serial No. 2017-530976, Office Action dated Jul. 3, 2018", w/ English translation, 7 pgs.
"Japanese Application Serial No. 2017-530976, Response filed Oct. 3, 2018 to Office Action dated Jul. 3, 2018", w/ English Claims, 12 pgs.
"Singaporean Application Serial No. 11201701540P, Written Opinion dated Nov. 7, 2018", 6 pgs.
"Singaporean Application Serial No. 11201701540P, Written Opinion dated Dec. 28, 2017", 7 pgs.
Ali, Khademhosseini, et al., "Micromolding of photoelectrically hyaluronic acid for cell encapsulation and entrapment", Journal of Biomedical Materials Research Part A, vol. 79A, No. 3, (Jan. 1, 2006), 522-532.
Alireza, Dolatshahi Pirouz, et al., "A combinatorial cell-laden gel microarray for inducing osteogenic differentiation of human mesenchymal stem cells", Scientific Reports, vol. 4, (Jan. 29, 2014), 2 pgs.

(56) References Cited

OTHER PUBLICATIONS

Anke, Tukker, "Is the time right for in vitro neurotoxicity testing using human iPSC-derived neurons?", Alternatives to Animal Experimentation: ALTEX, (Jan. 1, 2016).
Blau, Axel, "Cell adhesion promotion strategies for signal transduction", Current Opinion in Colloid and Interface Science 18, (2013), 12 pages.
Booth, Ross, et al., "Characterization of microfluidic in vitro model of the blood-brain barrier", Lab on Chip Royal Society of Chemistry vol. 12, No. 10, (Jan. 1, 2012), 1784-1792.
Braam, et al., "Inhibition of ROCK improves survival of human embryonic stem cell-derived cardiomyocytes after dissociation", Annals of the New York Academy of Science,1188, (2010), 52-57 pgs.
Brewer, G J, et al., "Gold-Coated Microelectrode Array With Thiol Linked Self-Assembled Monolayers for Engineering Neuronal Cultures", IEEE Transactions on Biomedical Engineering vol. 51 No. 1, (Jan. 1, 2004), 158-165.
Claverol-Tinture, E, et al., "Multi electrode arrays with elastomeric microstructured overlays for extracellular recordings from patterned neurons", Communication; Journal of Neural Engineering, Institute of Physics Publishing, Bristol, GB, vol. 2, No. 2,, (Jun. 1, 2005), L1-L7.
Dib-Hajj, Sulayman D, et al., "Human pain in a dish: Native DRG neurons and differentiated pluripotent stem cells", IASP PAIN 155, (Sep. 2014), 1681-1682.
Dolatshahi-Pirouz, Alireza, et al., "A combinatorial cell-laden gel microarray for inducing osteogenic differentiation of human mesenchymal stem cells", Scientific Reports, (Jan. 29, 2014), 1-9.
Fernandes, et al., "High-throughput cellular microarray platforms: applications in drug discovery, toxicology and stem cell research", Trends in Biotechnology, 27(6), (2009), 342-349.
Garcia-Parra, et al., "Modeling neural differentiation on micropatterned substrates coated with neural matrix components", Frontiers in Cellular Neuroscience vol. 6, (Mar. 14, 2012), 1-12.
Gi, Seok Jeong, et al., "Networked neural spheroid by neuro-bundle mimicking nervous system created by topology effect", Molecular Brain, Biomed Central Ltd, London UK, vol. 8, No. 1 (Mar. 22, 2015), 17.
Hayder, Amin, et al., "Electrical Responses and Spontaneous Activity of Human iPS-Derived Neuronal Networks Characterized for 3-month Culture with 4096-Electrode Arrays", Frontiers in Neuroscience, vol. 10, (Mar. 30, 2016).
Heller, D, et al., "Patterned networks of mouse hippocampal neurons on peptide-coated gold surfaces", Biomaterials vol. 26, No. 8, (Mar. 1, 2005), 883-889.
Jack, Wang D, et al., "Organization of Endothelial Cells, Pericytes, and Astrocytes into 3D Microfluidic in Vitro Model of the Blood-Brain Barrier", Molecular Pharmaceutics, vol. 13 No. 3, (Mar. 7, 2016), 895-906.
Jacquelyn, Brown, et al., "Recreating blood-brain barrier physiology and structure on chip novel neurovascular microfluidic bioreactor", Biomicrofluidics, vol. 9 No. 5, (Sep. 1, 2015), 16 pgs.
Kathe, Stanness, et al., "Morphological and functional characterization of an in vitro blood-brain barrier model", Brain Research vol. 771 No. 2, (Oct. 1, 1997), 329-342.
Kim, Yong Hee, et al., "In vitro extracellular recording and stimulation performance", Journal of Neural Engineering, (Nov. 24, 2015), 10 pgs.
Krinke, Dana, et al., "A microelectrode-based sensor for label-free in vitro detection of ischemic effects on cardiomyocytes", Biosensors and Bioelectronics vol. 24, No. 15, (May 15, 2009), 2798-2803.
Luca, Cucullo, et al., "Development of a Humanized In Vitro Blood?Brain Barrier Model to Screen for Brain Penetration of Antiepileptic Drugs", EPILEPSIA, vol. 48 No. 3, New York US, (Mar. 1, 2007), 505-516.
Maher, et al., "The neurochip: a new multielectrode device for stimulating and recording from cultured neurons", Journal of Neuroscience Methods vol. 87 No. 1, (Feb. 1, 1999), 45-56.
Maher, M, et al., "A microstructure for interfacing with neurons: the neurochip", Engineering in Medicine and Biology Society,1998. Proceedings of the20th Annual International Conference of the IEEE, IEEE—Piscataway, NJ, US, vol. 4, (Oct. 29, 1998), 1698-1702.
Mohammad, A Kaisar, et al., "New experimental models of the blood-brain barrier for CNS drug discovery", Expert Opinion on Drug Discovery, (Nov. 7, 2016), 89-103.
Mordwinkin, et al., "A Review of Human Pluripotent Stem Cell-Derived Cardiomyocytes for High-Throughput Drug Discovery, Cardiotoxicity Screening and Publication Standards", Journal of Cardiovascular Translational Research, 6(1), (2013), 22-30.
Musick, Katherine, et al., "Three-dimensional micro-electrode array for recording dissociated neuronal cultures", Lab Chip., (Feb. 9, 2010), 18 pgs.
Naik, Pooja, et al., "In Vitro Blood Brain Barrier Models: Current and Perspective Technologies", J Pharm Sci, (Apr. 2012), 30 pgs.
Nichol, J W, et al., "Cell-laden microengineered gelatin methacrylate hydrogels", Biomaterials Elsevier Science Publishers BV Barking GB vol. 31, No. 21, (Jan. 7, 2010), 5536-5544.
Nichol, Jason W., et al., "Cell-laden microengineered gelatin methacrylate hydrogels", National Institutes of Health, (Jul. 31, 2010), 1-20.
Panke, O, et al., "A cell-based impedance assay for monitoring transient receptor potential (TRP) ion channel activity", Biosensors and Bioelectronics vol. 26 No. 5, (Jan. 15, 2011), 2376-2382.
Paradis, Alexandre, et al., "Optimization of an nvitro human blood brain barrier model", Methods X 3, (2016), 25-34.
Peppas, Nicholas A., et al., "Hydrogels in Biology and Medicine: From Molecular Principles ot Bionanotechnology", Advanced Materials, (2006), 1345-1360.
Salisbury, David, "Blood brain barrier on a chip sheds new light on silent killer", News.Vanderbilt EDU, [Online] Retrieved from the internet: <https://news.vanderbilt.edu/2016/12/06/blood-brain-barrier-on-a-chip-sheds-new-light-on-silent-killer/>, (Dec. 6, 2016), 6 pgs.
Wong, et al., "Advancing Microarray Assembly with Acoustic Dispensing Technology", Analytical Chemistry, 81, (Jan. 1, 2009), 509-514 pgs.
"U.S. Appl. No. 14/839,170, Notice of Allowability dated Oct. 17, 2019", 3 pgs.
"U.S. Appl. No. 14/839,170, Notice of Allowance dated Jun. 10, 2019", 10 pgs.
"U.S. Appl. No. 14/839,170, Notice of Allowance dated Oct. 2, 2019", 8 pgs.
"U.S. Appl. No. 14/839,170, Response filed Apr. 30, 2019 to Final Office Action dated Jan. 30, 2019", 10 pgs.
"U.S. Appl. No. 15/293,563, Advisory Action dated Jun. 19, 2019", 5 pgs.
"U.S. Appl. No. 15/293,563, Examiner Interview Summary dated Oct. 9, 2019", 4 pgs.
"U.S. Appl. No. 15/293,563, Non Final Office Action dated Aug. 29, 2019", 13 pgs.
"U.S. Appl. No. 15/293,563, Response filed Jun. 3, 2019 to Final Office Action dated Apr. 3, 2019", 6 pgs.
"U.S. Appl. No. 15/293,563, Response filed Aug. 5, 2019 to Advisory Action dated Jun. 19, 2019", 6 pgs.
"U.S. Appl. No. 15/374,961, Advisory Action dated Sep. 30, 2019", 6 pgs.
"U.S. Appl. No. 15/374,961, Final Office Action dated Jun. 13, 2019", 17 pgs.
"U.S. Appl. No. 15/374,961, Response filed Sep. 12, 2019 to Final Office Action dated Jun. 13, 2019", 7 pgs.
"U.S. Appl. No. 15/789,335, Non Final Office Action dated Jul. 26, 2019", 21 pgs.
"European Application Serial No. 15762878.5, Response Filed Sep. 13, 2019 to Communication Pursuant to Article 94(3) EPC dated Nov. 20, 2018", 7 pgs.
"European Application Serial No. 16829018.7, Communication Pursuant to Article 94(3) EPC dated May 28, 2019", 6 pgs.
"Japanese Application Serial No. 2018-519441, Notification of Reasons for Refusal dated May 14, 2019", W/ English Translation, 5 pgs.

(56) References Cited

OTHER PUBLICATIONS

"Japanese Application Serial No. 2018-519441, Response Filed Aug. 14, 2019 to Notification of Reasons for Refusal dated May 14, 2019", w/English Claims, 9 pgs.
"Japanese Application Serial No. 2018-530058, Notification of Reasons for Refusal dated Jul. 9, 2019", With English Translation, 12 pgs.
"Modeling pain with rat dorsal root ganglion neurons on MEAs", Axion Biosystems, [Online] Retrieved from the internet: <https://www.axionbiosystems.com/sites/default/files/resources/modeling_pain_with_rat_dorsaLroot_ganglion_neurons_on_meas.pdf>, (2014), 8 pgs.
Claverol Tinture, E, et al., "Communication; Multielectrode arrays with elastomeric microstructured overlays for extracellular recordings from patterned neurons; Communication", Journal of Neural Engineering, vol. 2, No. 2, (Jun. 1, 2005), pp. L1-L7.
Hazeltine, Laurie B, et al., "Engineering the human pluripotent stem cell microenvironment to direct cell fate", NIH Public Access: Author Manuscript, Published in Final Edited Form as Biotechnology Advances, vol. 31, Issue 7, (2013), 38 pgs.
Walsh, Frank, et al., "Artificial backbone neuronal network for nano scale sensors", IEEE Conference on Computer Communications Workshop. Shanghai, (2011), 449-454.
U.S. Appl. No. 16/738,408, filed Jan. 9, 2020, Method of Fabricating Cell Arrays and Uses Thereof.
U.S. Appl. No. 16/922,475, filed Jul. 7, 2020, Method of Manufacturing or Differentiating Mammalian Pluripotent Stem Cellsor Progenitor Cells Using a Hollow Fiber Bioreactor.
"U.S. Appl. No. 14/839,170, Corrected Notice of Allowability dated Mar. 20, 2020", 5 pgs.
"U.S. Appl. No. 15/293,563, Examiner Interview Summary dated Dec. 26, 2019", 3 pgs.
"U.S. Appl. No. 15/293,563, Notice of Allowance dated Mar. 25, 2020", 12 pgs.
"U.S. Appl. No. 15/293,563, Response filed Dec. 26, 2019 to Non-Final Office Action dated Aug. 29, 2019", 9 pgs.
"U.S. Appl. No. 15/374,961, Non-Final Office Action dated Mar. 17, 2020", 17 pgs.
"U.S. Appl. No. 15/789,335, Final Office Action dated Mar. 3, 2020", 29 pgs.
"U.S. Appl. No. 15/789,335, Response filed Aug. 27, 2020 to Final Office Action dated Mar. 3, 2020", 11 pgs.
"U.S. Appl. No. 16/321,908, Non-Final Office Action dated Aug. 21, 2020", 8 pgs.
"European Application Serial No. 15762878.5, Communication Pursuant to Article 94(3) EPC dated Feb. 6, 2020", 5 pgs.
"European Application Serial No. 16829018.7, Communication Pursuant to Article 94(3) EPC dated Dec. 20, 2019", 6 pgs.
"European Application Serial No. 16829018.7, Response filed Dec. 6, 2019 to Communication Pursuant to Article 94(3) EPC dated May 28, 2019", 9 pgs.
"Japanese Application Serial No. 2018-519441, Notification of Reasons for Refusal dated Jan. 7, 2020", with English translation, 8 pages.
"Japanese Application Serial No. 2018-530058, Examiners Decision of Final Refusal dated Apr. 21, 2020", with English translation, 18 pages.
"Japanese Application Serial No. 2018-530058, Response filed Nov. 13, 2019 to Notification of Reasons for Refusal dated Jul. 9, 2019", with English claims, 13 pages.
"Singaporean Application Serial No. 11201701540P, Response filed Mar. 18, 2019 to Written Opinion dated Nov. 7, 2018", 15 pgs.
Jalil, M. A., et al., "Molecular network topology and reliability for multipurpose diagnosis", International Journal of Nanomedicine, 6, (Oct. 18, 2011), 2385-2392.
Kong, F., et al., "Automatic Liquid Handling for Life Science: A Critical Review of the Current State of the Art", Journal of Laboratory Automation, 17(3), (Feb. 6, 2012), 169-185.
Veiseh, M, et al., "Short peptides enhance single cell adhesion and viability on microarrays", Langmuir. 23, (2007), 26 pages.
"U.S. Appl. No. 16/922,475, Preliminary Amendment filed Nov. 20, 2020", 5 pgs.
"European Application Serial No. 15762878.5, Response filed Nov. 17, 2020 to Communication Pursuant to Article 94(3) EPC dated Feb. 6, 2020", 7 pgs.
"U.S. Appl. No. 15/374,961, Final Office Action dated Dec. 28, 2020", 20 pgs.
"Photografting", [online]. Wikipedia(r) [retrieved on Jan. 13, 2021]. Retrieved: https: en.wikipedia.org wiki Photografting, (edited Jan. 30, 2015), 1 pg.
"Photomask", [online] Wikipedia(r) [retrieved Jan. 13, 2021], Retrieved from the Internet: https: en.wikipedia.org wiki Photomask, (edited Jan. 1, 2021), 5 pgs.
"U.S. Appl. No. 15/789,335, Non Final Office Action dated Apr. 29, 2021", 29 pgs.
"U.S. Appl. No. 15/789,335, Response filed Jul. 28, 2021 to Non Final Office Action dated Apr. 29, 2021", 9 pgs.
"U.S. Appl. No. 16/323,118, Response filed Jun. 30, 2021 to Restriction Requirement dated Mar. 31, 2021", 9 pgs.
"U.S. Appl. No. 16/323,118, Restriction Requirement dated Mar. 31, 2021", 6 pgs.
"European Application Serial No. 15762878.5, Communication Pursuant to Article 94(3) EPC dated Jul. 13, 2021", 4 pgs.
Davidson, S, et al., "Human sensory neurons: Membrane properties and sensitization by inflammatory mediators", Pain 155, (2014), pp. 1861-1870.
Fan, C, et al., "Effect of type-2 astrocytes on the viability of dorsal root ganglion neurons and length of neuronal processes", Neural Regeneration Research 9(2), (2014), 10 pages.
McConnell, E R, et al., "Evaluation of multi-well microelectrade array for neurotoxicity screening using a chemical training set", NeuroToxicology 33, (2012), pp. 1048-1057.
Romero-Sandoval, E A, et al., "Neuroimmune interactions and pain: Focus on glial-modulating targets", Curr. Opin. Investig. Drugs 9(7), (2008), 16 pages.
"U.S. Appl. No. 15/789,335, Final Office Action dated Sep. 2, 2021", 35 pgs.
"U.S. Appl. No. 16/323,118, Non Final Office Action dated Sep. 15, 2021", 6 pgs.

* cited by examiner

SURFACE ENERGY DIRECTED CELL SELF ASSEMBLY

CROSS-REFERENCE TO RELATED APPLICATIONS

This application claims the benefit of the filing date of U.S. application Ser. No. 62/186,670, filed on Jun. 30, 2015, the disclosure of which is incorporated by reference herein.

BACKGROUND

Contact angle is one of the common ways to measure the wettability of a surface or material. Wetting refers to the study of how a liquid deposited on a solid (or liquid) substrate spreads out or the ability of liquids to form boundary surfaces with solid states. The wetting is determined by measuring the contact angle, which the liquid forms in contact with the solids or liquids. The wetting tendency is larger, the smaller the contact angle or the surface tension is. A wetting liquid is a liquid that forms a contact angle with the solid, which is smaller than about 90°. A non-wetting liquid creates a contact angle from between 90° to 180° with the solid.

The contact angle is an angle that a liquid creates with a solid surface or capillary walls of a porous material when both materials come in contact together. This angle is determined by both properties of the solid and the liquid and the interaction and repulsion forces between liquid and solid and by the three phase interface properties (gas, liquid and solid). Cohesion and adhesion forces that are intermolecular forces describe those interactions. The balance between the cohesive forces of similar molecules such as between the liquid molecules (i.e., hydrogen bonds and Van der Waals forces) and the adhesive forces between dissimilar molecules such as between the liquid and solid molecules (i.e., mechanical and electrostatic forces) will determine the contact angle created in the solid and liquid interface. The traditional definition of a contact angle is the angle a liquid creates with the solid or liquid when it is deposited on it. Contact angle is defined by Young's equation that is shown in FIG. 1.

However in practice it is better to refer to FIG. 2 which shows how a water based liquid will behave when applied to a surface where there are both hydrophobic and hydrophilic patterns pre-deposited onto a carrier such as glass, metal or plastic.

SUMMARY

The present disclosure provides for high and low solid surface free energy patterns to contain and direct a cell solution to form micro 3 dimensional structures that mimic mammalian tissue topography such as heart, musculoskeletal, and liver organs.

In one embodiment, the present disclosure provides a method of fabricating cell arrays on a carrier where the surface energy of the carrier has been modified and patterned so that only areas of low contact angle are wet by a water based cell solution. The patterned cell solution, e.g., a stem cell solution, when applied to the carrier surface then self assembles into a 3 dimensional micro pattern on the carrier that mimics the surface topography of mammalian organs. In one embodiment, induced pluripotent stem cells that differentiate into cardiomyocytes are applied to a carrier with a pre patterned high contact angle ink and only the low contact angle areas of the carrier are wet and form 3 dimensional structures which induce the cells to beat with regularity on the carrier surface.

The present disclosure thus provides a method of forming micro 3 dimensional cell, e.g., stem cell, arrays on a carrier surface by utilizing pre-defined (predetermined) printed ink patterned into 2 dimensional coating geometries deposited onto a carrier such as glass, plastic or metal.

Also provided is a method of fabricating cell, e.g., stem cell, arrays on a carrier surface where the pre-defined (predetermined) surface energy patterns direct the cell solution to self-assemble into a micro 3 dimensional geometry.

Further provided is a method of fabricating cell, e.g., stem cell, arrays on a carrier surface where the pre-defined surface energy patterns have a contact angle with water of greater than 90 degrees and in one embodiment greater than 120 degrees.

More particularly, the present disclosure shows a method of utilizing pluripotent stem cell derived cardiomyocytes that can be patterned into linear arrays utilizing pre-defined surface energy geometric patterns, wherein the cells subsequently beat in rhythm after deposition onto a carrier surface.

These and other advantages of the disclosure will become apparent to those of reasonable skill in the art from the following detailed description, as considered in conjunction with the following examples and drawings.

DETAILED DESCRIPTION

The following discussion is directed to various embodiments of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

In the embodiments disclosed herein, the surface energy of a substrate is modified before depositing a cell liquid (e.g., an ink), e.g., a stem cell liquid, thereon. The term "surface energy" refers to a property of a material that draws surface molecules inward. In some embodiments, the surface energy of the substrate carrier surface on which the cell liquid is to be deposited is modified so as to approximately match the surface energy (surface tension) of the cell liquid itself. By approximately matching the surface's surface energy to that of the cell liquid, the cell liquid adheres to the desired regions and does not adhere to the remaining regions which may have a much lower surface energy or higher contact angle. In other embodiments, the surface energy of the regions on which the cell liquid is not to adhere is modified to reduce its surface energy. Then, when the cell liquid coats the substrate surface, the liquid adheres only to the regions whose surface energy was not reduced. These embodiments are described in greater detail below.

The embodiments described herein permit the formation of 3-D cell, e.g., stem cell differentiated cells, into geometries (e.g., as thin as 250 microns or smaller) to be formed on a substrate and formed at ambient conditions. Further, the substrate material used may include silicon, glass, acrylate, polyimide, elastomers, polycarbonate, polyethylene terephthalate (PET), and the like. The substrate may be rigid or flexible if desired.

As used herein, the term "pattern" is generally used to refer to the desired pattern of the living cells formed by the cell liquid. The pattern may include straight lines (e.g., a set of spaced, parallel lines) or any arbitrary pattern or 3-D formation of cellular material.

Figure 3:
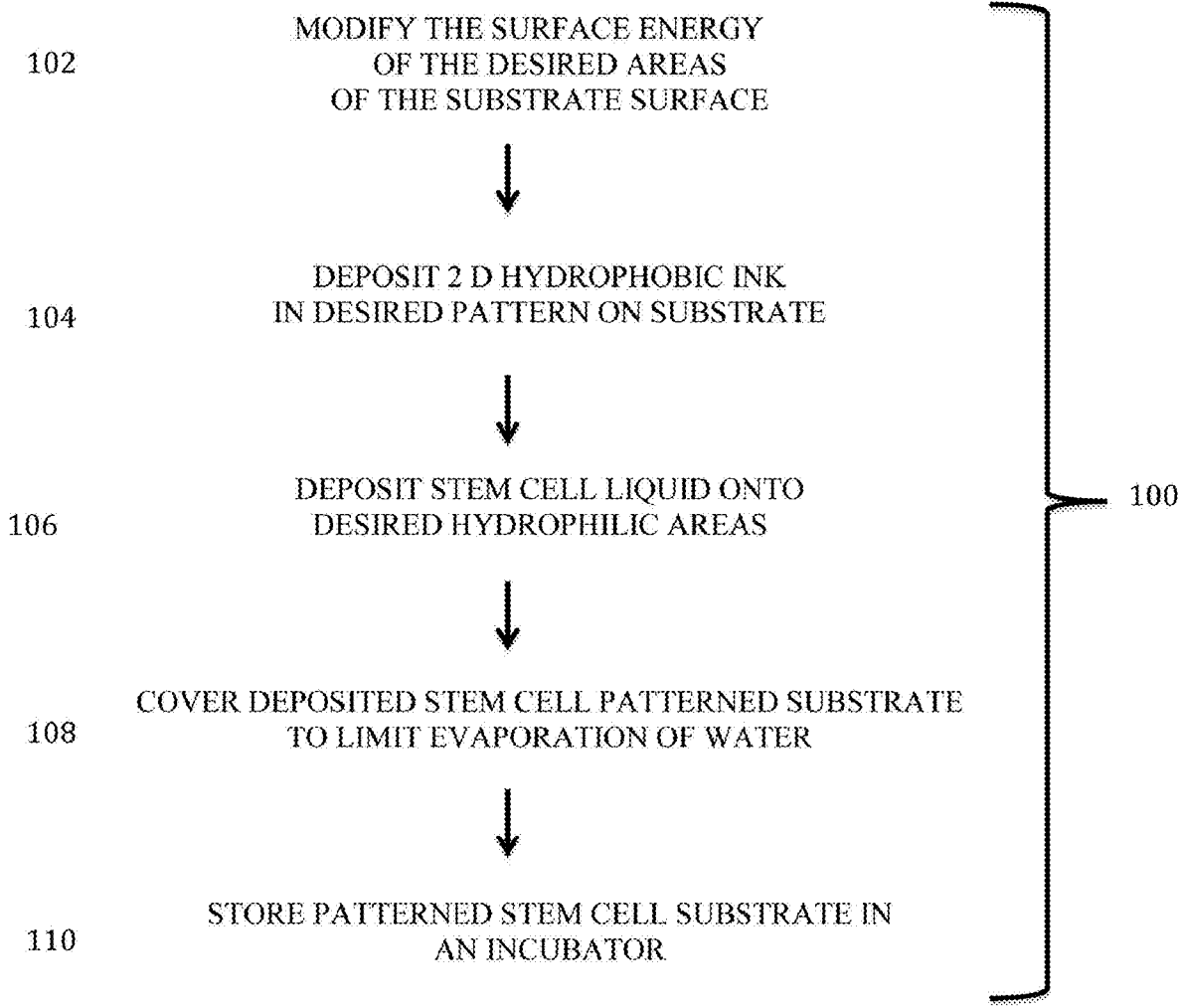
FIG. 3 shows a method in accordance with one embodiment.

FIG. 3 illustrates an embodiment of the method 100 in which the surface energy of areas of the substrate is modified to approximate the surface energy of the cell liquid. The substrate areas so modified are the areas where the cell material formed from the cell liquid is to remain thereby forming cell pathways across the substrate. To the extent possible, some of the actions depicted in FIG. 3 may be performed in a different order from that shown and some actions may be performed in parallel, not sequentially.

Figure 1:
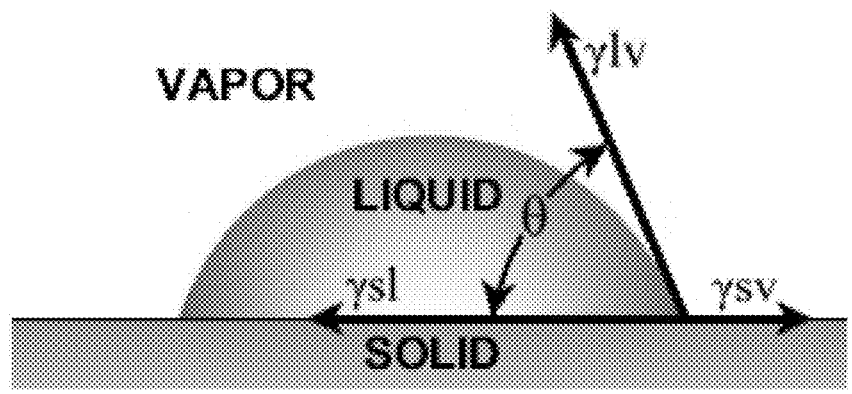
FIG. 1 shows the how to mathematically describe contact angle.
Figure 2:
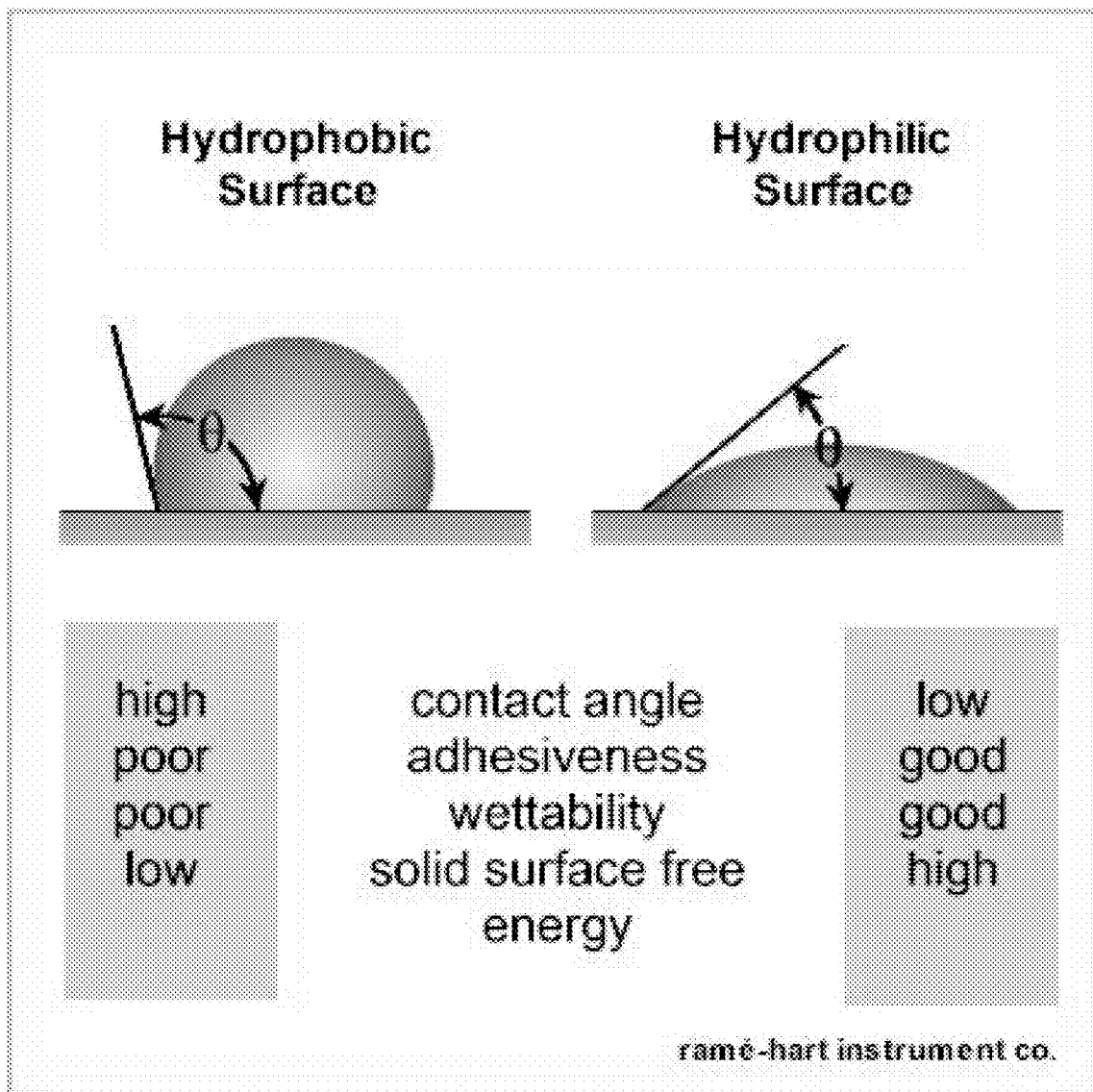
FIG. 2 shows a comparison between hydrophobic and hydrophilic contact angles.

At 102, the method comprises altering the surface energy of the desired areas of the substrate surface (e.g., the areas in which cell material is desired to be formed). Depositing, on the substrate surface, a substance such as a super hydrophobic ink so as to increase the water contact angle from below 90 degrees to over 115 degrees and for example greater than 120 degrees, can perform this action. In some embodiments, the deposited material has a water contact angle of about 120 to about 160 degrees. A suitable material to deposit on the substrate surface includes fluorinated polymers available from Cytonix Inc. Altering the surface energy of the desired areas may entail decreasing the surface energy of those areas of the substrate surface by at least 20%, 25%, 30%, 35%, 40%, 45%, 50% or more. FIG. 2 depicts a side view of a substrate 130.

Figure 4:
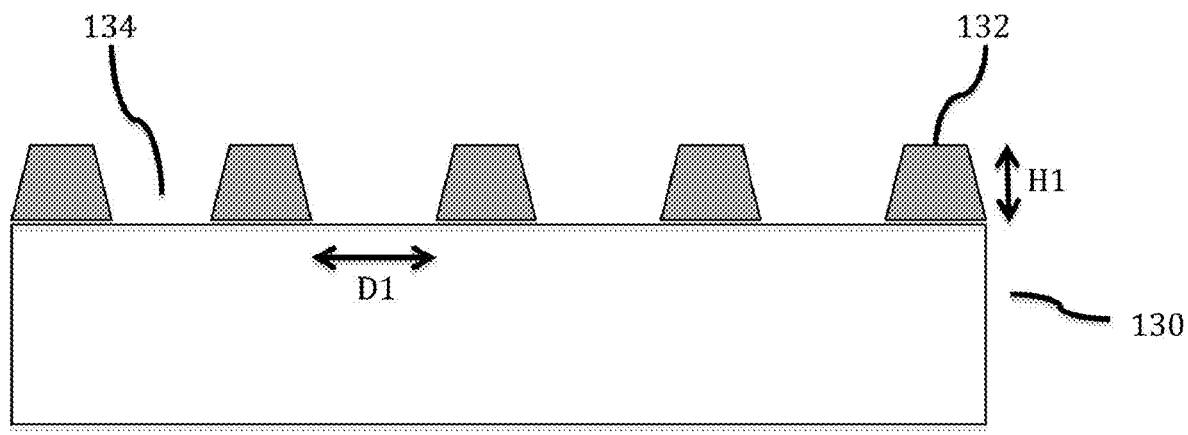
FIG. 4 shows a substrate with various 2-D hydrophobic structures deposited thereon.

At 104, the method comprises depositing a cell doped liquid that spontaneously forms into micro three-dimensional (3-D) structures on the surface in the hydrophilic untreated regions of the surface of the substrate. Such structures may be of any shape or size. In some embodiments, such structures can take on any shape as determined by the high and low energy pattern deposited onto the surface such as lines, squares, triangles, or any polygon type structure. FIG. 4 shows a side view of the substrate 130 on which 2-D super hydrophobic ink patterns 132 are deposited. The 2-D structures 132 form valleys 134 there between. The surface energy of the 2-D structures may approximate the surface energy of the altered regions of the substrate and may in one embodiment be formed of fluoroacrylate as well. In some embodiments, the surface energy of the 2-D structures 132 is within 2%, 5%, 10%, 12% or 15% of the surface energy of the substrate surface.

The 2-D structures 132 comprise raised or protruding structures that delimit the width and shape of the desired cell pattern. In some embodiments, the structures 132 may have a height (H1) of 250 microns (or about 100 to 200, 200 to 300 or 300 to 400 microns) a width of 50 microns (or about 25 to 50, 50 to 75, 75 to 100, 100 to 250 microns or more) and a distance (D1) between ridges of 50 microns (or about 25 to 50, 50 to 75, 75 to 100, 100 to 200, or 200 to 500 microns or more). The structures may also have a height of a few nanometers to several hundred microns. The distance D1 defines the pitch of the cell pattern.

At 106, the method comprises depositing a cell doped liquid (e.g., an ink) on to the desired areas. The cell liquid chosen in this step should have a surface energy (surface tension) approximately equal to the surface energy of the unaltered regions of the substrate 134. In some embodiments, the cell liquid has a surface contact angle of less than 90 degrees and in one embodiment less than 50 degrees. In some embodiments, the liquid's surface contact angle may be less than 35 degrees. The cell liquid in one embodiment is a mixture of growth factors, nutrients, and adhesion promoters that are easily dispensed by techniques well known in the art. For example, the cell liquid may be a cardiomyocytes mixed with the appropriate aforementioned additives. In some embodiments, the depositing (printing) of the cell liquid is performed using an inkjet printer, or automated pipetting system. The print gap, ink volume, print speed, etc. are adjustable based on the application at hand and thus may be varied as desired.

Figure 5:
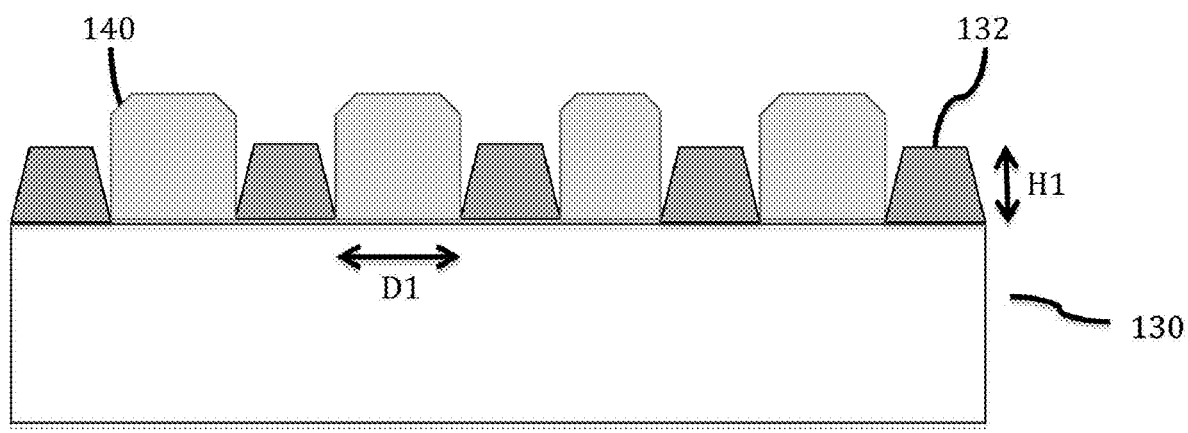
FIG. 5 illustrates stem cell material deposited in the valleys between the 2-D ink of FIG. 4 in accordance with various embodiments.

FIG. 5 shows that the cell doped liquid 140 readily settles into the valleys 134 between the predefined super hydrophobic printed ink patterns. The close match between the surface energy of the substrate and that of the cell liquid causes the liquid 140 to settle in the valleys in a generally constant depth fashion. Because the surface energy of the substrate 130 and 2-D structures 132 is not excessively low, the cell liquid does not form beads. Because the surface energy of the substrate is not too high, the liquid does not spread too quickly. If the surface energy of the substrate was too high, the liquid would likely cover and adhere to the tops of the 2-D structures 132 themselves which would be undesirable in some cases.

At 108 in FIG. 3, the method further comprises forming a seed stem cell layer using the deposited stem cell liquid. This action can be performed by allowing the deposited stem cell liquid to settle (e.g., for a few hours) on the substrate and allow the stem cells to adhere to the surface. At 110 in FIG. 3 the now formed stem cell plate is then placed into an incubator to facilitate cell growth and viability.

EXAMPLES

The following examples are provided to illustrate the exemplary methods for practicing the present invention.

Example 1. iPS-derived cardiomyocytes were deposited onto two surface modified glass slides as in FIG. 3. The predefined hydrophilic wells had the same area of the ones on a standard 96-well plate (about 0.32 $cm^2$). The wells were seeded with 600,000 live cells/$cm^2$, meaning, 1.92E+05live cells/well. Three adhesion promoter materials, matrigel vs. gelatin/fibronectin vs. laminin were used as substrate cell binding options.

Example 2. The stem cell doped liquid was seeded with iPS-derived cardiomyocytes at the same density and conditions on an 8-well plastic (Permanox) standard chamber slide to see how they would compare as a reference standard.

The slides together with a 6 $cm^2$ empty plate containing tissue culture-grade water were all placed inside a large 15 $cm^2$ tissue culture dish to create an additional saturated atmosphere to avoid too much evaporation.

One day after seeding the cells were attached in all the wells. It appeared that there were more cells rounded up in the patterned slide vs. the unpatterned chamber slide. From the aforementioned examples it appears that using glass is not optimal for binding iPS based cardiomyocytes and so polymer based substrates may be employed to facilitate good cell adhesion and growth to hydrophobic and hydrophilic patterned substrates.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method to prepare a substrate containing cells in a pattern, consisting of: a) providing a substrate having a surface coated with a material selected from the group consisting of matrigel, gelatin, fibronectin, laminin, and a combination of gelatin and fibronectin, the surface energy of a portion of which is modified with a hydrophobic liquid composition consisting of fluorinated polymers that are applied to the surface in a geometric pattern and remains in the pattern as a result of the difference in the surface energy between the hydrophobic liquid composition and the surface of the substrate; and b) applying to the geometrically patterned substrate a population of cells selected from the group consisting of mammalian stem cells and cardiomyocytes in a liquid water based composition, wherein the geometrically patterned substrate results in the mammalian stem cells or cardiomyocytes accumulating in portions of the surface of the substrate that do not include the hydrophobic liquid composition, thereby providing a substrate containing mammalian stem cells or cardiomyocytes in a pattern.

2. The method of claim 1 wherein the cells in the population of cells are mammalian stem cells.

3. The method of claim 2 wherein the mammalian stem cells are induced pluripotent stem cells.

4. The method of claim 1 wherein the cells in the population of cells are cardiomyocytes.

5. The method of claim 1 wherein the substrate material is formed of silicon, glass, acrylate, polyimide, elastomers, polycarbonate, or polyethylene terephthalate (PET).

6. The method of claim 1 wherein the modification of the portion of the surface with the hydrophobic liquid composition increases the contact angle from below 90 degrees to over 115 degrees.

7. The method of claim 1 wherein the modification of the portion of the surface with the hydrophobic liquid composition increases the contact angle from about 120 to about 160 degrees.

8. The method of claim 1 wherein the portions of the surface that include the liquid, water based composition have a contact angle of less than 90 degrees.

9. The method of claim 1 wherein the portions of the surface that include the liquid, water based composition have a contact angle of less than 50 degrees.

10. The method of claim 1 wherein the portions of the surface that include the liquid, water based composition have a contact angle of less than 35 degrees.

11. The method of claim 1 wherein the liquid, water based composition on the surface of the substrate has a contact angle of less than 90 degrees.

12. The method of claim 1 wherein the liquid, water based composition on the surface of the substrate has a contact angle of less than 50 degrees.

13. The method of claim 1 wherein the liquid, water based composition on the surface of the substrate has a contact angle of less than 35 degrees.

14. The method of claim 1 wherein one or more growth factors, nutrients, or adhesion promoters are in the liquid water based composition.

15. A method to prepare a substrate containing cells in a pattern, consisting of applying a population of mammalian induced pluripotent stem cells or cardiomyocytes in a liquid water based composition to a surface of a substrate coated with fibronectin or laminin, and geometrically patterned with a composition consisting of fluorinated polymers, wherein the geometrically patterned substrate results in the mammalian induced pluripotent stem cells or cardiomyocytes accumulating in portions of the surface of the substrate that do not include the fluorinated polymers, thereby providing a substrate containing cells in a pattern.

16. The method of claim 15 wherein the surface of the substrate that does not include the hydrophobic liquid composition is coated with fibronectin.

17. The method of claim 15 wherein the surface of the substrate that does not include the hydrophobic liquid composition is coated with laminin.

* * * * *